(12) United States Patent
Legora et al.

(10) Patent No.: US 6,979,672 B2
(45) Date of Patent: Dec. 27, 2005

(54) CYCLOSPORIN-BASED PHARMACEUTICAL COMPOSITIONS

(75) Inventors: Michela Legora, Como (IT); Federico Mailland, Milan (IT)

(73) Assignee: Polichem, S.A., Luxembourg (LU)

(*) Notice: Subject to any disclaimer, the term of this patent is extended or adjusted under 35 U.S.C. 154(b) by 108 days.

(21) Appl. No.: 10/327,646

(22) Filed: Dec. 20, 2002

(65) Prior Publication Data
US 2004/0121944 A1 Jun. 24, 2004

(51) Int. Cl.$^7$ ............................................. A61K 38/00
(52) U.S. Cl. ........................... 514/11; 514/11; 514/2; 514/58; 424/486; 424/450; 424/451
(58) Field of Search ............................... 514/11, 2, 15; 424/486, 450, 451

(56) References Cited

U.S. PATENT DOCUMENTS

| | | |
|---|---|---|
| 2,865,859 A | 12/1958 | Lubowe |
| 3,678,149 A | 7/1972 | Prigal |
| 4,388,307 A | 6/1983 | Cavanak |
| 4,474,761 A | 10/1984 | Caen et al. |
| 4,612,193 A | 9/1986 | Gordon et al. |
| 4,649,047 A | 3/1987 | Kaswan |
| 4,659,696 A | 4/1987 | Hirai et al. |
| 4,670,419 A | 6/1987 | Uda et al. |
| 4,711,902 A | 12/1987 | Serno |
| 4,722,914 A | 2/1988 | Drye et al. |
| 4,839,342 A | 6/1989 | Kaswan |
| 4,990,337 A | 2/1991 | Kurihara et al. |
| 5,314,685 A | 5/1994 | Tyle et al. |
| 5,338,761 A | 8/1994 | Nakajima et al. |
| 5,342,625 A | 8/1994 | Hauer et al. |
| 5,589,455 A | 12/1996 | Woo |
| 5,733,572 A * | 3/1998 | Unger et al. ............... 424/450 |
| 5,739,105 A | 4/1998 | Kim et al. |
| 5,756,450 A | 5/1998 | Hahn et al. |
| 5,773,572 A * | 6/1998 | Fishleigh et al. ........... 530/324 |
| 5,977,066 A | 11/1999 | Cavanak |
| 5,980,939 A | 11/1999 | Kim et al. |
| 6,294,192 B1 * | 9/2001 | Patel et al. ............... 424/451 |
| 2002/0107183 A1 | 8/2002 | Petszulat et al. |

FOREIGN PATENT DOCUMENTS

| | | |
|---|---|---|
| CH | 641 356 A5 | 2/1984 |
| CN | 641 356 A5 | 2/1984 |
| DE | 29 07 460 | 9/1979 |
| DE | 39 24 207 A1 | 1/1990 |
| DE | 39 24 207 01 | 1/1990 |
| DE | 39 30 928 A1 | 3/1990 |
| DE | 40 03 844 A1 | 8/1990 |
| DE | 40 05 190 A1 | 8/1990 |
| DE | 40 05 0190 A1 | 8/1990 |
| EP | 0 094 157 A1 | 11/1983 |
| EP | 0 143 305 A1 | 6/1985 |
| EP | 0 170 623 A2 | 2/1986 |
| EP | 0365044 A3 | 4/1990 |
| EP | 0 327 280 B1 | 3/1992 |
| EP | 0 697 881 B1 | 12/2002 |
| FR | 2 642 650 | 3/1990 |
| GB | 2 015 339 | 9/1979 |
| GB | 2 228 198 A | 8/1990 |
| GB | 2 230 440 A | 10/1990 |
| WO | 94/23733 | 10/1994 |
| WO | WO 98/40051 A1 | 9/1998 |
| WO | WO 01/12229 A1 | 2/2001 |

OTHER PUBLICATIONS

Smith, D., Microemulsions, pp. 299–314.
Sandimmune Product Information, Novartis, Mar. 2002.
Lutrol F 127 Technical Information, Polaxamer 407, Thickening agent and gel former for the pharmaceutical industry, BASF, Apr. 1999.
Oleochemicals –IMWITOR Fatty Acids Derivatives, online product information, Sasol, 2001.
Petszulat et al., publ. apl. no. US 202/0107183 A1 (Aug. 8, 2002).
Smith, D., Microemulsions, pp. 299–314.
Sandimmune Product Information, Novartis, Mar. 2002.
Lutrol F 127 Technical Information, Polaxamer 407, Thickening agent and gel former for the pharmaceutical industry, BASF, Apr. 1999.
Oleochemicals–Imwitor Fatty Acids Derivatives, online product information, Sasol, 2001.

* cited by examiner

Primary Examiner—Christopher R. Tate
Assistant Examiner—B. Dell Chism
(74) Attorney, Agent, or Firm—Kenyon & Kenyon

(57) ABSTRACT

A pharmaceutical formulation for the oral administration of cyclosporin is described, which formulation is capable of providing substantially constant and foreseeable plasma levels of the active ingredient. The formulation has the following quali-quantitative composition by weight:

Figure 1:
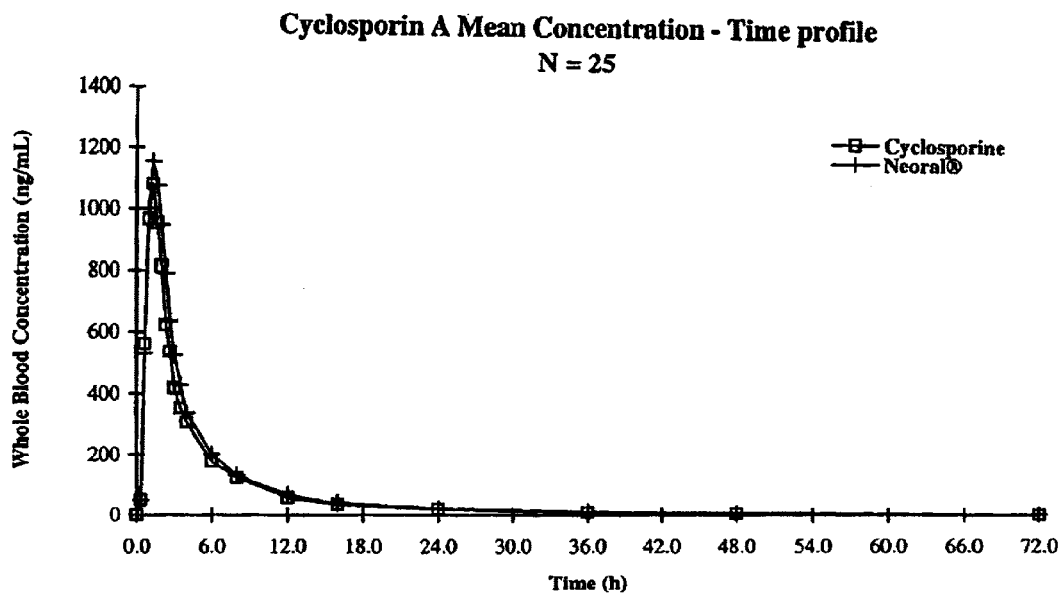

(a) cyclosporin in the amount of from about 8 to about 12% of the total weight;

(b) ethanol in the amount of from about 12 to about 18% of the total weight;

(c) a polyoxyethylene/polyoxypropylene block copolymer in the amount of from about 8 to about 12% of the total weight;

(d) water in the amount of from about 4 to about 6% of the total weight;

(e) a solubilizer having an HLB from 13 to 15 in the amount of from about 28 to about 40% of the total weight;

(f) an ester of a $C_1$–$C_6$ alkyl alcohol and a $C_{14}$–$C_{18}$ saturated fatty acid in the amount of from about 20 to about 30% of the total weight.

20 Claims, 2 Drawing Sheets

CYCLOSPORIN-BASED PHARMACEUTICAL COMPOSITIONS

The present invention relates to a pharmaceutical formulation for the oral administration of cyclosporin, which formulation is capable of providing substantially constant and foreseeable plasma levels of the active ingredient.

BACKGROUND OF THE INVENTION

Cyclosporin is a drug having immunosuppressant activity, which is used to prevent graft rejection in transplant patients and for the treatment of a series of autoimmune diseases characterized by an abnormal reaction of the immune system. The clinical availability of cyclosporin has greatly improved the prognosis of transplant patients, considerably increasing their survival. However, the drug has an intrinsic toxicity which limits its therapeutic window, requiring the achievement of defined plasma levels. Outside the therapeutic window the patient's life is threatened, both when plasma levels attained are lower than those needed—due to lack of efficacy and the consequent increased risk of rejection—and when plasma levels exceed the safe levels—due to the specific risk of toxicity, particularly renal and/or liver toxicity.

In its therapeutic use as an immunosuppressant, cyclosporin is currently administered either orally or by injection. However, since the solubility of cyclosporin in water is extremely low, (e.g. 20 µg/ml to 30 µg/ml), an oily solution containing ethanol has been recognized to be a suitable vehicle. Even so, the bioavailability of oral preparations of cyclosporin is extremely low, generally below 30%. This is believed to be due to the separation of cyclosporin as a solid immediately after it comes into contact with water, e.g. in the mouth and on contact with gastric fluids.

It is generally accepted that cyclosporin cannot be absorbed following oral administration unless it is first solubilized in gastrointestinal fluids by appropriate excipients.

The first cyclosporin formulations available for therapeutic use (SANDIMMUN®) were characterized by a high degree of intra- and interindividual variability with respect to absorption, so that it was necessary to frequently titrate the plasma levels in the individual patients in order to continuously adjust the administered dosage.

Subsequently, in order to avoid the described disadvantage, and thus to obtain less variable plasma levels of the drug, formulations that are based on preconcentrates for microemulsions and that have demonstrated less individual variability, or compositions that are difficult to produce and just as complex, were described. One of those formulations, (in the form of a preconcentrate for a microemulsion) was introduced onto the market (NEORAL®) as an improvement over the previous oily solution of cyclosporin in ethanol.

The prior art is rich in complex compositions which, nevertheless, lead to absorption profiles of the active ingredient which are extremely variable in quantitative terms.

U.S. Pat. No. 4,388,307, relating precisely to SANDIMMUN®, describes a cyclosporin-based composition containing (a) a non-ionic ester of a triglyceride and a polyalkylene polyol, (b) a saturated fatty acid triglyceride, and (c) a mono- or di-glyceride having improved physical and absorption properties.

U.S. Pat. No. 5,047,396 discloses an intravenous pharmaceutical formulation composed of a) 1 part by mass of one or more cyclosporins, b) 8 to 13 parts by mass of a monoester of a saturated hydroxylated fatty acid formed with polyethylene glycol or the mixture of said monoesters, c) 4 to 10 parts by mass of one or more intravenously administerable mono- or polivalent alcohols.

U.S. Pat. No. 5,756,450 discloses a combination of cyclosporin and a water soluble monoester of a saturated or unsaturated fatty acid and a polyol, especially a saccharide.

German patent application DE-4418115 discloses an at least ternary vehicle formed by the transesterification product of a vegetable oil and mono-, di- or triglyceride of oleic acid and/or linoleic acid, and/or of polyoxyethylenated vegetable oil, propylene glycol and ethanol.

U.S. Pat. No. 5,342,625, which relates to NEORAL®, describes a composition which allows a more homogeneous absorption of the active ingredient by means of a formulation which consists of a preconcentrate for microemulsion, that does not contain alkanols.

U.S. Pat. No. 5,639,724 discloses pharmaceutical compositions comprising a cyclosporin as active ingredient, a fatty acid triglyceride, a glycerol fatty acid partial ester or propylene glycol or sorbitol complete or partial ester, preferably, and a tenside having an HLB of at least 10, without ethanol.

U.S. Pat. No. 6,258,808 describes a composition containing a cyclosporin, 1,2-propylene glycol, a mixed mono-, di- and tri-glyceride and a hydrophilic surfactant.

U.S. Pat. No. 6,420,355 discloses a pharmaceutical composition in the form of an emulsion preconcentrate for oral administration and containing a cyclosporin. The pharmaceutical composition has a carrier medium for the cyclosporin that contains a hydrophilic organic solvent; a mixed mono-, di-, and tri-glyceride or a transesterified and polyethoxylated vegetable oil; and a polyoxyethylene-sorbitan-fatty acid ester surfactant.

U.S. Pat. No. 4,990,337 relates to a pharmaceutical composition comprising a cyclosporin in admixture with a monoglyceride or diglyceride of a $C_6$–$C_{10}$ fatty acid in an amount sufficient to dissolve the cyclosporin.

U.S. Pat. No. 5,589,455 discloses a microemulsion free from ethanol and containing (1) cyclosporin as the active ingredient; (2) polyethylene glycol having a molecular weight from 200 to 600 Da as cosurfactant; (3) a mixture comprising the esterification product of a fatty acid and a primary alcohol, the triglyceride of a medium-chain fatty acid nd the monoglyceride of a fatty acid; and (4) a surfactant having an HLB value from 10 to 17.

United States patent application US2002/0107183A1 describes a pharmaceutical composition containing (a) cyclosporin as the active ingredient, (b) an alkylene polyether and/or an alkylene polyester as vehicles, in which the HLB of component (b) is at least 10.

Pharmaceutical compositions containing water insoluble active ingredients are also disclosed in US2002120015, WO02/45696, WO00/37050, WO96/03113 and WO00/03753.

DESCRIPTION OF THE INVENTION

The object of the present invention is to provide a novel orally administrable formulation based on cyclosporin, which formulation, unlike SANDIMMUN®, is capable of providing substantially constant and foreseeable plasma levels and is at least bioequivalent to NEORAL®.

The formulation according to the present invention contains the following components in the following proportions by weight:

(a) cyclosporin in the amount of from about 8 to about 12% of the total weight;

(b) ethanol in the amount of from about 12 to about 18% of the total weight;

(c) a polyoxyethylene/polyoxypropylene block copolymer in the amount of from about 8 to about 12% of the total weight;

(d) water in the amount of from about 4 to about 6% of the total weight;

(e) a solubilizer having an HLB from 13 to 15 in the amount of from about 28 to about 40% of the total weight;

(f) the ester of a $C_1$–$C_6$ alkyl alcohol and $C_{14}$–$C_{18}$ saturated fatty acids in the amount of from about 20 to about 30% of the total weight;

where the sum of compounds (a), (b), (c), (d), (e) and (f) is 100%.

Preferably, the cyclosporin is cyclosporin A.

Component (c), that is to say, the polyoxyethylene/polyoxypropylene block copolymer, is preferably poloxamer 407 (CAS No. 9003-11-6) which is marketed by BASF under the mark Lutrol® F 127 and whose use for the preparation of transmucosal release formulations is described in international patent application WO 94/03157.

As regards component (e), that is to say, the solubilizer, it preferably has an HLB value from 13.5 to 14.5 and, even more preferably, it is caprylocaproyl macrogol-8-glyceride (CAS No. 85536-07-8 and 84963-88-2). This is a mixture of mono-, di- and triesters of glycerol and of PEG 400 with medium-chain fatty acids ($C_8$–$C_{10}$) which is marketed, for example, by Gattefossé under the mark Labrasol®; Labrasol® has an HLB value of 14 and has the following composition by weight:

| | |
|---|---|
| $C_8$–$C_{10}$ monoglycerides | approximately 4%; |
| $C_8$–$C_{10}$ diglycerides | approximately 17%; |
| $C_8$–$C_{10}$ triglycerides | approximately 6%; |
| $C_8$–$C_{10}$ monoesters of PEG 400 | approximately 14%; |
| $C_8$–$C_{10}$ diesters of PEG 400 | approximately 36%; |
| free PEG 400 | approximately 20%; |
| free glycerol | approximately 3%. |

For the purposes of the present invention, with the term solubilizer it is intended a component in a mixture which is able to enhance the affinity to the solvent of a molecule which is poorly soluble in that solvent.

As regards component (f), that is to say, the ester of a $C_1$–$C_6$ alkyl alcohol and $C_{14}$–$C_{18}$ saturated fatty acids, it is preferably isopropyl myristate.

In the more preferred embodiment, the ratios range from about 9% to about 11% for cyclosporin, from about 9% to about 11% for poloxamer 407, from about 13.5% to about 16.5% for ethanol, from about 4.5% to about 5.5% for water, from about 31.5% to about 38.5% for caprylocaproyl macrogol-8-glyceride and finally from about 22.5% to about 27.5% for isopropyl myristate; even more preferably, they are about 10% for cyclosporin, about 15% for ethanol, about 5% for water, about 10% for poloxamer 407, about 35% for caprylocaproyl macrogol-8-glyceride and about 25% for isopropyl myristate.

The formulation according to the present invention can be obtained by dissolving cyclosporin in ethanol at room temperature; the poloxamer 407, the water, the caprylocaproyl macrogol-8-glyceride and, the isopropyl myristate are then added, under stirring; after 10 to 20 minutes the mixture is heated to a temperature from 25 to 55° C. (preferably from 25 to 45°, even more preferably from 25 to 35° C.) and maintained at that temperature, under stirring, for a period from 80 to 120 minutes; then is cooled to room temperature (approximately 21–24° C.) The thus-obtained mixture is then filled into soft gelatin capsules under stirring. The process for the preparation of the present formulation constitutes a further subject of the invention.

Contrarily to the formulations known in the art, that according to the present invention is neither an emulsion, nor a microemulsion, nor a preconcentrate for microemulsions: it is a biphasic system consisting of two visibly separated mixtures, one lipophilic and one hydrophilic, wherein the concentration of cyclosporin is substantially equal between the two phases.

The preferred pharmaceutical form for the administration of the medicament is a soft gelatin single-dose capsule in which the liquid biphasic system is homogeneously distributed.

As will be appreciated from the following Examples, which have only an illustrative and non-limiting purpose, the formulation according to the present invention has surprisingly demonstrated a bioavailability in animals and humans equivalent to the commercial reference formulation, which is based on a preconcentrate for microemulsion.

EXAMPLE 1

A cyclosporin formulation having the following composition by weight is prepared:

| | |
|---|---|
| 1. cyclosporin A | 10% |
| 2. ethanol | 15% |
| 3. water | 5% |
| 4. Lutrol ® F 127 | 10% |
| 5. Labrasol ® | 35% |
| 6. isopropyl myristate | 25%. |

Cyclosporin is dissolved in ethanol at room temperature. The remaining excipients are added under stirring in the order listed above. The mixture so obtained is heated to 50° C. in order to permit the complete dissolution of the components and is subsequently cooled down to room temperature. The bulk mixture is filled into soft gelatin capsules under stirring.

EXAMPLE 2

A preparation of cyclosporin A in 100 mg capsules (formulation A), which were obtained by the same method as that indicated in Example 1, was orally administered to beagle dogs in comparison with other preparations in capsules containing 100 mg of cyclosporin A which were formulated either as commercial preconcentrates for microemulsion (formulation B, NEORAL®), or as commercial oily solutions of cyclosporin in ethanol (formulation C, SANDIMMUN®) or with an excipient based on polyethylene glycols, glycerophosphorylcholine and ethanol (formulations D and E), respectively. The study was carried out on four animals, each one receiving all formulations. In all cases the formulation was administered at a dose of one capsule per animal, equal to 100 mg of cyclosporin in fast conditions.

Blood samples were withdrawn before administration and 0.5, 1, 1.5, 2, 4, 6, 8, 24 hours after oral administration and were analysed by an LC/MS method for the content of cyclosporin A. The calculated parameters were the time ($t_{max}$) to reach the maximum plasma concentration ($C_{max}$) and the area under time-concentration curve ($AUC_{0-t}$) by means of the trapezoidal method according to standard methodology.

The results are given in the following Table (mean data±SD)

|  | Formulation | | | | |
| --- | --- | --- | --- | --- | --- |
|  | A | B | C | D | E |
| tmax h | 1.1 | 1.0 | 1.0 | 3.4 | 2.1 |
| Cmax ng/mL | 727.4 | 1,192.9 | 578.0 | 28.0 | 59.1 |
| AUC ng.h/mL | 4,356.2 | 4,852.5 | 3,132.9 | 461.8 | 518.3 |

In conclusion, the bioavailability of the preparation forming the subject of the present invention (formulation A) was found to be comparable to that of the commercial reference preparation consisting of a preconcentrate for microemulsion (formulation B, NEORAL®) and greater than all the other tested formulations.

EXAMPLE 3

A biostudy was carried out on healthy volunteers with the aim of comparing the bioavailability of a 100 mg cyclosporin capsules, obtained by the same method as that indicated in Example 1, with that of a commercially available reference product (NEORAL®, USA) consisting of a preconcentrate for microemulsion, (cyclosporin100 mg capsules). Either product was randomly administered at the dose of 2 capsules (200 mg) per volunteer, simultaneously in the morning in fasting conditions, on two different occasions separated by 14 day washout.

Blood samples were obtained as per standard procedure before treatment and at the following times: 0.33, 0.67, 1, 1.33, 1.67, 2, 2.33, 2.67, 3, 3.5, 4, 6, 8, 12, 16, 24, 36, 48 and 72 hours after the administration of the drug. The concentration of cyclosporin in the whole blood was measured by the LC/MS method. The pharmacokinetic analysis and the statistical analysis were carried out using standard procedures. The analysis of bioequivalence was carried out on the ln-transformed values of $AUC_{0-t}$, $AUC_{0-\infty}$ and $C_{max}$.

Mean blood level profiles of the 25 subjects who completed the experiment are reported in FIG. 1. ANOVA was performed on ln-transformed values, and ratios of least-squares means and 90% geometric confidence intervals were within 80% and 125% for all the considered parameters. Therefore the formulation of the present invention is bioequivalent to the commercial reference preparation (NEORAL®) based on preconcentrate for microemulsion

EXAMPLE 4

A biostudy in fed conditions was carried out on healthy volunteers with the aim of comparing the bioavailability of a 100 mg cyclosporin capsules, obtained by the same method as that indicated in Example 1, with that of a commercially available reference product (NEORAL®, USA) consisting of a preconcentrate for microemulsion, (100 mg capsules). Either product was randomly administered at the dose of 2 capsules (200 mg) per volunteer, simultaneously in fed conditions, on two different occasions separated by 14 day washout.

Blood samples were obtained as per standard procedure before treatment and at the following times: 0.33, 0.67, 1, 1.33, 1.67, 2, 2.33, 2.67, 3, 3.5, 4, 6, 8, 12, 16, 24, 36, 48 and 72 hours after the administration of the drug. The concentration of cyclosporin in the whole blood was measured by the LC/MS method. The pharmacokinetic analysis and the statistical analysis were carried out using standard procedures. The bioequivalence analysis was carried out on the ln-transformed values of $AUC_{0-t}$, $AUC_{0-\infty}$ and $C_{max}$.

Figure 2:
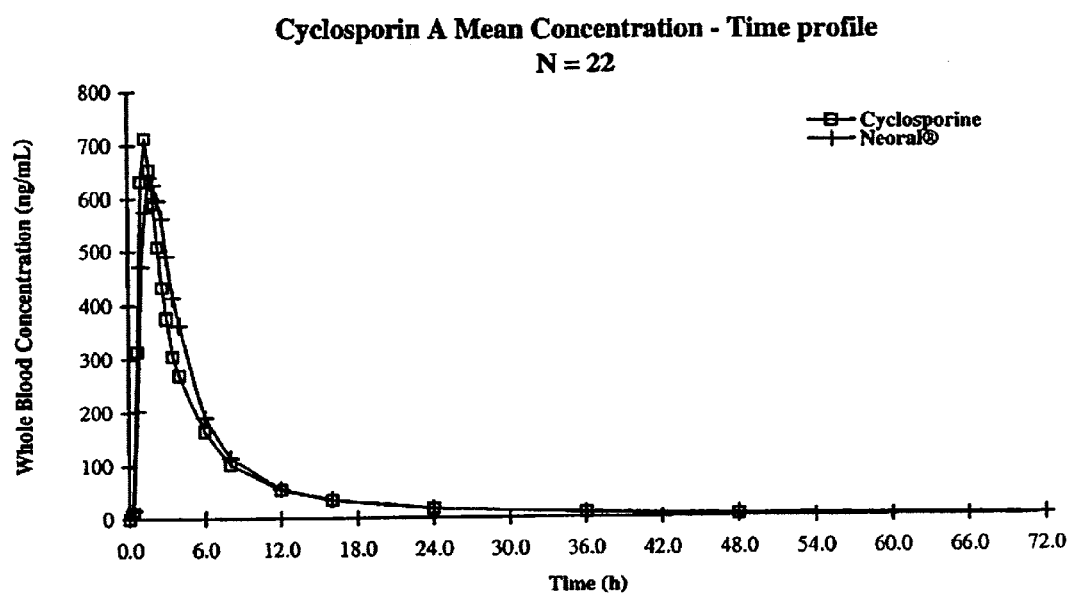

Mean blood level profiles of the 22 subjects who completed the experiment are reported in FIG. 2.

ANOVA was performed on ln-transformed values, and ratios of least-squares means were within the acceptance range of 80% to 125% for all the considered parameters. Therefore the formulation of the present invention is bioequivalent to the commercial reference preparation (NEORAL®) based on a preconcentrate for microemulsion, even in fed conditions.

We claim:

1. A pharmaceutical formulation of compounds (a)–(f) for oral administration comprising by weight:
   (a) cyclosporin in the amount of from about 8 to about 12% of the total weight;
   (b) ethanol in the amount of from about 12 to about 18% of the total weight;
   (c) a polyoxyethylene/polyoxypropylene block copolymer in the amount of from about 8 to about 12% of the total weight;
   (d) water in the amount of from about 4 to about 6% of the total weight;
   (e) a solubilizer having an hydrophilic lipophilic balance (HLB) from 13 to 15 in the amount of from about 28 to about 40% of the total weight; and
   (f) an ester of a $C_1$–$C_6$alkyl alcohol and a $C_{14}$–$C_{18}$ saturated fatty acid in the amount of from about 20 to about 30% of the total weight.

2. A pharmaceutical formulation according to claim 1, wherein the cyclosporin is cyclosporin A.

3. A pharmaceutical formulation according to claim 1, wherein the polyoxyethylene/polyoxypropylene block copolymer is poloxamer 407.

4. A pharmaceutical formulation according to claim 1, wherein the solubilizer has an HLB of from 13.5 to 14.5.

5. A pharmaceutical formulation according to claim 1, wherein the solubilizer is caprylocaproyl macrogol-8-glyceride.

6. A pharmaceutical formulation according to claim 1, wherein the ester of a $C_1$–$C_6$ alkyl alcohol and a $C_{14}$–$C_{18}$ saturated fatty acid is isopropyl myristate.

7. A pharmaceutical formulation according to claim 1, wherein the cyclosporin is present in an amount of from about 9% to about 11%.

8. A pharmaceutical formulation according to claim 1, wherein the ethanol is present in an amount of from about 13.5% to about 16.5%.

9. A pharmaceutical formulation according to claim 1, wherein the polyoxyethylene/polyoxypropylene block copolymer is present in an amount of from about 9% to about 11%.

10. A pharmaceutical formulation according to claim 1, wherein the water is present in an amount of from about 4.5% to about 5.5%.

11. A pharmaceutical formulation according to claim 1, wherein the solubilizer is present in an amount of from about 31.5% to about 38.5%.

12. A pharmaceutical formulation according to claim 6, wherein the isopropyl myristate is present in an amount of from about 22.5% to about 27.5%.

13. A pharmaceutical formulation according to claim 1, wherein the cyclosporin is cyclosporin is present in an amount of about 10%, the ethanol is present in an amount of about 15%, the water is present in an amount of about 5%, the polyoxyethylene/polyoxypropylene block copolymer is present in an amount of about 10%, the solubilizer having an HLB from 13 to 15 is present in an amount of about 35% and the ester of a alkyl alcohol and a $C_{14}$–$C_{18}$ saturated fatty acid is present in an amount of about 25%:

14. A pharmaceutical formulation according to claim 1, wherein the cyclosporin is cyclosporin A, the polyoxyethylene/polyoxypropylene block copolymer is poloxamer 407, the solubilizer is caprylocaproyl macrogol-8-glyceride and the ester of the $C_1$–$C_6$ alkyl alcohol and the $C_{14}$–$C_{18}$ saturated fatty acid is isopropyl myristate, having the following composition by weight:
   (a) cyclosporin A in an amount of about 10% of the total weight;
   (b) ethanol in an amount of about 15% of the total weight;
   (c) poloxamer 407 in an amount of about 10% of the total weight;
   (d) water in an amount of about 5% of the total weight;
   (e) caprylocaproyl macrogol-8-glyceride in an amount of about 35% of the total weight; and
   (f) isopropyl myristate in an amount of about 25% of the total weight.

15. A pharmaceutical formulation according to claim 1 in the form of a biphasic system comprising two visibly separated mixtures.

16. Soft gelatin capsules containing a pharmaceutical formulation according to claim 1.

17. A process for the preparation of a pharmaceutical formulation according to claim 1, comprising: (1) dissolving compound (a) in compound (b) at room temperature to form a mixture; (2) adding compounds (c), (d), (e) and (f) under stirring to the mixture; (3) heating the mixture after 10 to 20 minutes to a temperature range from about 25 to about 55° C. (4) maintaining the mixture within said temperature range, under stirring for from about 80 to about 120 minutes; and (5) cooling said mixture to room temperature.

18. A process for the preparation of the soft gelatin capsules according to claim 16, comprising: (1) dissolving compound (a) in compound (b) at room temperature to form a mixture; (2) adding compounds (c), (d), (e) and (f) under stirring to the mixture; (3) heating the mixture after 10 to 20 minutes to a temperature range from 25 to 55° C. (4) maintaining the mixture within said temperature range, under stirring for from about 80 to about 120 minutes; and (5) cooling said mixture to room temperature, wherein the mixture is filled into the soft gelatin capsules under stirring.

19. A pharmaceutical formulation obtained according to the process of claim 17.

20. Soft gelatin capsules obtained according to the process of claim 18.

* * * * *